United States Patent [19]

Yee et al.

[11] Patent Number: 5,108,287

[45] Date of Patent: Apr. 28, 1992

[54] AUTOCLAVABLE DRILL BIT CONTAINER

[76] Inventors: Nancy Yee, 1150 18th St., Suite 101, Santa Monica, Calif. 90403; Yasuo Otake, 2107 Holmby Ave., Los Angeles, Calif. 90025

[21] Appl. No.: 755,522

[22] Filed: Sep. 5, 1991

[51] Int. Cl.⁵ .............................. A61G 15/00
[52] U.S. Cl. ............................ 433/77; 206/369; 206/379
[58] Field of Search ............. 433/77; 206/368, 369, 206/379

[56] References Cited

U.S. PATENT DOCUMENTS

| | | | |
|---|---|---|---|
| 2,971,637 | 2/1961 | Simons | 206/369 |
| 3,018,876 | 1/1962 | Huot | 206/379 |
| 3,092,443 | 6/1963 | Dietz | 433/77 |
| 3,248,167 | 4/1966 | Friedman | 206/369 |
| 3,904,035 | 9/1975 | Metzler et al. | 206/379 |
| 4,256,457 | 3/1981 | Behring | 433/77 |
| 4,397,395 | 8/1983 | McKelvey | 206/369 |
| 4,503,972 | 3/1985 | Nelligan et al. | 206/369 |
| 5,006,066 | 4/1991 | Rouse | 433/77 |

Primary Examiner—John J. Wilson
Attorney, Agent, or Firm—Beehler & Pavitt

[57] ABSTRACT

An autoclavable container for drill bits and/or burs comprising a narrow rectangular block having vertical orifices extending partially downwardly from its upper face, and a U-shaped cover having a pair of legs extending downwardly from a transverse member to slidably encompass the end walls of the block and a pair of orifices side shields extending downwardly from the transverse member and spaced apart from each other to house the heads of the drill bits and/or burs extending upwardly from the block orifices, each of the end walls of the block having a boss or projection, and each of the inner walls of the legs having a pair of interconnected recesses adopted to receive the boss or projection in the end wall of the block so that the block may be moved from a first upper position secured within the cover, to a second lower position at which it may be pivoted outwardly to a third position providing access to the block orifices for insertion or removal of the burs or drill bits.

7 Claims, 2 Drawing Sheets

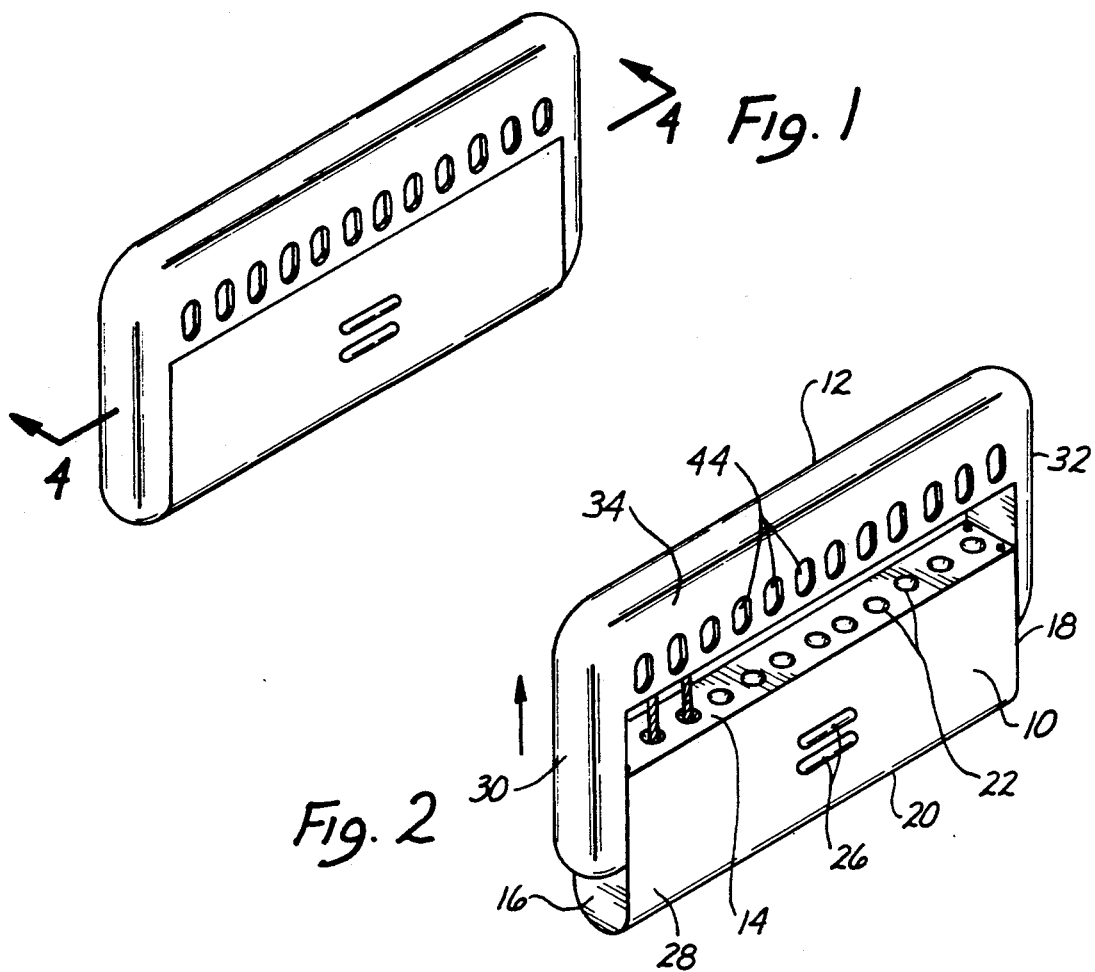

AUTOCLAVABLE DRILL BIT CONTAINER

FIELD OF THE INVENTION

This invention relates generally to the field of autoclaving equipment and, particularly, to containers for dental burs and/or drill bits which are to be placed in an autoclave.

BACKGROUND OF THE INVENTION

In the ordinary course of performing dental work upon a patient, a dentist may use as many as half a dozen drill bits and/or burs to make different kinds of cuts, holes and seats for inlays and/or bridges and to effect the smoothing of undesired rough edges, scarps, points, etc. Since these operations seldom result in immediate damage to the drill bit or bur, these instruments can be used again and again, either on the same patient, or on different patients. However, because the human mouth can be a breeding ground or repository for bacteria and viruses, a drill bit or bur, after being used on one patient's mouth, should not be used in the mouth of another patient without having first been carefully autoclaved. This has become particularly important with the possibility that acquired immune deficiency (AIDS) viruses can be passed from one patient to another through use of the same dental instruments upon successive patients, where such instruments have not been thoroughly autoclaved.

However, because dental drill bits and burs are normally quite small, providing suitable means for handling drill bits and burs for and during the autoclaving process, has long been a problem and various inventors have attempted to provide devices for this purpose, as evidenced by the patents to M. W. Dietz, U.S. Pat. No. 3,092,443; M. R. Genis, U.S. Pat. No. 4,050,894; D. H. Kazen, U.S. Pat. No. 4,253,830; A. Nisii, U.S. Pat. No. 4,327,060; T. H. McKelvey, U.S. Pat. No. 4,397,395; C. A. Brewer, U.S. Pat. No. 4,959,199; M. R. Rouse, U.S. Pat. No. 5,006,066; and S. Castellini, U.S. Pat. No. 5,022,858.

While the inventors of each of these patents have addressed the matter of providing a suitable container in different ways, none of them appears to provide all the desired features and for all of the functional requirements for an autoclavable container for dental burs and drill bits. Among these requirements and desired features are:

1) Convenience in inserting and removing the burs and/or bits;

2) Securing the actual holding receptacle in such a manner as to prevent any possible spilling out of any of the burs or bits;

3) Providing for free flow for the steam or liquid in the autoclave in and around the container burs and bits for minimum retention of heat by and in the container after the autoclaving process;

4) Convenience in securing the container before insertion in the autoclave;

5) Convenience in removing the burs and bits after the autoclaving process;

6) Minimizing the size of the container; and

7) Minimizing the cost of manufacturing and assembling the components of the container.

SUMMARY OF THE INVENTION

The foregoing listed desired features for a dental drill bit and bur holding container are provided for by the present invention which comprises a rectangular orificed drill holding block which is pivotably fitted within a U-shaped cover and may be moved from a first and upper position in which the burs and drill bit heads are securely encompassed by the cover, and a second lower position wherein the rectangular block may be pivoted outwardly from the cover to expose the heads of the burs and bits to enable them to be selectively removed from, or inserted into, the orifices in the rectangular block.

DESCRIPTION OF THE DRAWINGS

In the accompanying drawings,

FIG. 1 is a perspective view of the container of the present invention in its first enclosed position;

FIG. 2 is a view similar to FIG. 1 but showing the bit receiving block moved into its second position;

FIG. 3 is a perspective view of the container with its bit receiving block shown in its third and open position;

DESCRIPTION OF THE PREFERRED EMBODIMENT

Figure 5:
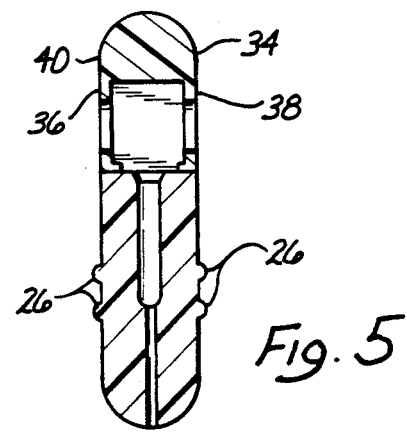
FIG. 5 is a section of the container taken on the line 5—5 of FIG. 4.
Figure 4:
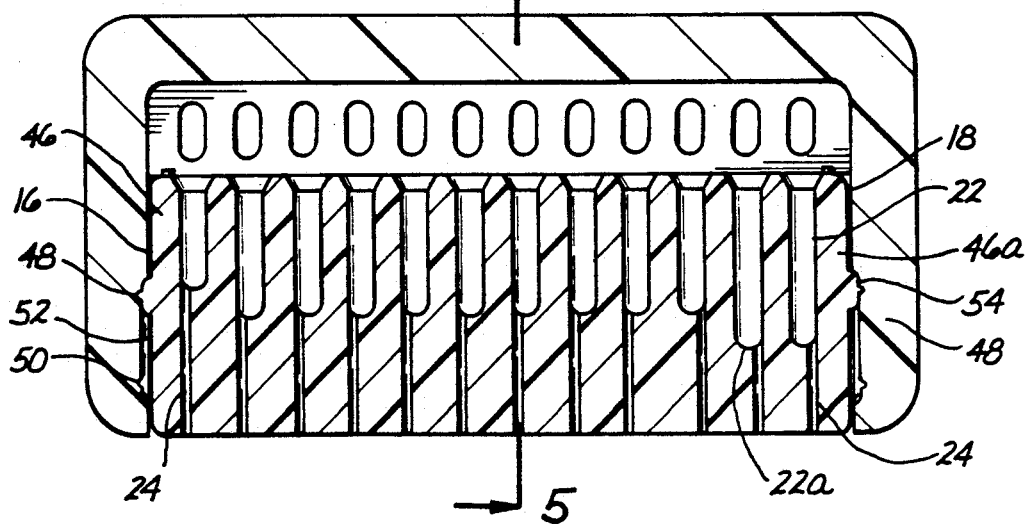
FIG. 4 is a vertical section of the container shown in FIG. 1 looking in the direction of the arrows 4—4 of FIG. 1.

Referring to the drawings, the container of the present invention comprises a bit receiving block 10 and a U-shaped cover 12. The block is essentially rectangular, having a top face 14, end walls 16 and 18 and a bottom 20 which is preferably rounded. A series of vertical orifices 22 are provided in the block 20 extending downwardly from its upper face 14 as best shown in FIGS. 4 and 5. These orifices may be varied in size to accommodate different lengths of burs and drill bits. Desirably, also, there should extend from the bottom 22a of each orifice 22 a smaller drainage passage 24. A pair of small ridges 26 to serve as grippers may also be provided on the side walls 28 of the block 10.

The cover 12 is preferably formed as an integrally molded U-shaped piece having a pair of legs 30, 32 connected by a transverse member 34. The transverse member not only connects the two legs 30, 32 but, in so doing, provides a pair of orificed side shields 36, 38 which extend down from the upper portion 40 of the transverse member 34 a distance at least as great as the maximum height of that portion of any drill bit or bur 42 which does not seat in an orifice 22 and, therefore, projects upwardly from the block face 14. Each side shield portion 36, 38 of the transverse member 34 has a series of cut-outs or orifices 44.

As best seen in FIG. 4, the inside wall 46, 46a of each leg 30, 32 respectively of the cover 12, is provided with two recesses 48, 50 which are inteconnected by a shallower channel 52. The recess 50 actually may be formed as a pair of interesecting channels 50a, 50b, with the channel 50b, in effect, being in line with, and slightly deeper than, the interconnecting channel 52. The purpose of the recesses 48 and 50 is to accommodate a boss 54 which is provided on each end wall 16 and 18 of the block 10.

The block 10 and the cover 12 desirably are both molded of a plastic material which may be subjected to steam or hot water at an autoclaving temperature of the order of 220 degrees Fahrenheit without deterioration. Desirably, also, the plastic of which the cover is formed, should be slightly resilient so that the legs 30 and 32 may be pulled apart from each other sufficiently to allow the block 10 with its end wall projections 54 to be forced in between the legs 30, 32 to where the projections 54 may be seated in the upper recesses 48 in the inner faces 46, 46a of the legs 30, 32 respectively.

Figure 1A:
FIG. 1a is an end view of the lower portion of the container.
Figure 2A:
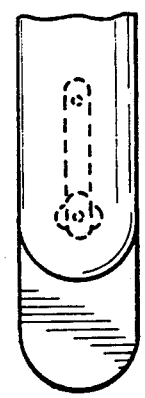
FIG. 2a is a partial end view of the container as shown in FIG. 2.

In use, when the block 10 is thus assembled with its cover 12, the block 10 is first forced downwardly so that its end wall projections 54 slide down the channels 52 to seat in the lower recesses 50. When so seated, the cover 12 may be rotated with reference to the block 10 to the position shown in FIG. 3 of the drawings. In this position, the assembly may be conveniently disposed on a table or tray, and drill bits or burs 42 may be inserted by their stems in the orifices 22. When it is desired to autoclave the drill bits or burs, the block 10 is first pivoted upwardly to the position shown in FIG. 2, and then moved upwardly with reference to the cover 12 to its first position shown in FIG. 1. The container with its drill bits may then be inserted in an autoclave for sterilization. It will be appreciated that the steam or autoclaving liquid will readily pass through the openings 44 in the side shields 36, 38 and about the upwardly projecting heads of the drill bits or burs, as well as around the shanks of the latter.

Figure 3A:
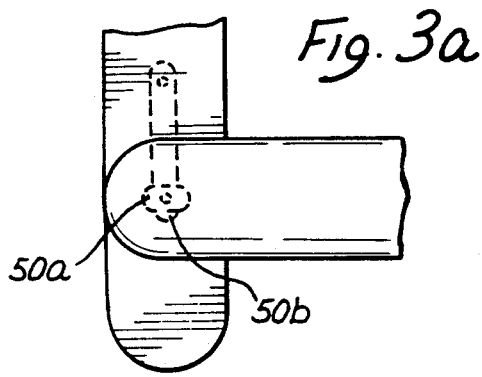
FIG. 3a is a partial end view of the container as shown in FIG. 3.

After being subjected to the autoclaving, the entire container may be removed and liquid in the passages 22 will drain out through the passages 24. When drainage has been completed, the block 10 may be pulled downwardly relative to the cover 12 by means of the grippers 26, first, to the second position shown in FIG. 2, and then pivoted to the third position shown in FIG. 3. The container, when thus positioned, as shown in FIG. 3, may be set on a dental tray or a shelf for easy access by the dentist or dental technician who may wish to remove any of the drill bits or burs 42.

It may be seen from the foregoing description, that the container of the present invention, thus meets all of the desired features for an autoclavable drill bit container.

We claim:

1. An autoclavable dental bur and bit container, said container comprising:

A. An elongated stem holder in the form of a narrow rectangular block, having a top face, a bottom, two side walls and two end walls extending between the top face and bottom, a plurality of vertical orifices extending down from the top face into the block, each orifice being dimensioned removably to receive the stem of a bur or bit and to leave exposed the bur or bit head, said block being formed of a material adapted to be subjected to water or steam heat of at least 220 degrees Fahrenheit without deformation or deterioration;

B. A U-shaped cover, said cover having a pair of legs with opposed inner walls spaced apart from each other by slightly greater than the distance between the end walls of the block, and having approximately the same width as said end walls, the upper ends of said legs being interconnected by a transverse bridging member having a width approximately equal of the width of the upper face of the block, said cover being disposed over the block with each leg of the cover having its inner wall adjacent one end wall of the block and the underside of the transverse member being spaced from the top side of the block by a distance at least as great as the height of the portions of the burs or bits which protrude above the upper face of the block, said cover further including a pair of thin orificed side shields each of which extends longitudinally between the cover legs and vertically between the transverse member and the upper face of the block, thereby covering said spacing between the transverse member and the block, the cover and its legs being formed of a resilient plastic material subjectable to steam heat of at least 220 degrees Fahrenheit without deterioration or permanent deformation;.

the inner wall of each leg in abutment with an end wall of the block having a first recess near but below the upper face of the block, and a second recess in the said inner wall spaced from and below the first recess by a distance at least slightly greater than the height of those portions of the burs or bits which protrude upwardly from the orifices in the block, said second recess being configured to permit at least partial rotation about an axis normal to said end wall, and extending through the recess in the inner wall of the other leg; and each end wall of the block having a projection located and configured to seat in the recesses in the legs abutting the end wall of the block when the cover is disposed over the block, thereby to removably retain the block in a first position in which the upper face of the block is in abutment with the lower edge of the shields and the end walls of the block are in abutment with the inner walls of the leg;

said block being slidable downwardly away from said cover by the application of a downward force, whereby the projections on the end walls of the block are forced out of the first recesses and down into the second recesses to dispose the block in a second position in which the block may be pivoted to a third position at an angle relative to the legs of the cover, thereby affording access to the upper face of the block to permit insertion of the dental burs or bits, into the orifices, or their withdrawal from said orifices.

2. The container as described in claim 1 wherein each of the orifices has a drain hole extending from its bottom to the outside of the block.

3. The container as described in claim 1 wherein the second orifice in the inner face of each leg is formed as a pair of short channels bisecting each other at an angle, with one channel being aligned subtantially vertically toward the first recess.

4. The container as described in claim 1 wherein each shield has a plurality of aligned openings thereby to permit steam or hot liquid to pass between the shields and in and around the dental burs or bits.

5. The container as described in claim 1 wherein the legs and transverse member are molded as a single piece.

6. The container as described in claim 1 wherein the upper face of the block is provided with bosses inward of its edges and the shields are formed to be snapped into their positions against said bosses.

7. The container as described in claim 1 wherein a channel extends between each first and second recess in the inner wall of the cover leg, thereby to facilitate the movement of the projection in the abutting block end wall between the first and second recess and correspondingly the movement of the block between its first and second positions.

* * * * *